United States Patent [19]
Murakami

[11] Patent Number: 5,736,352
[45] Date of Patent: Apr. 7, 1998

[54] METHOD AND APPARATUS FOR DETERMINATION OF THE ACTIVITY OF CHOLESTEROL OXIDASE AND METHOD AND APPARATUS FOR EVALUATION OF THE TOXICITY OF CHEMICAL SUBSTANCES

[75] Inventor: Toru Murakami, Tokyo, Japan

[73] Assignee: NEC Corporation, Tokyo, Japan

[21] Appl. No.: 603,776

[22] Filed: Feb. 20, 1996

[30] Foreign Application Priority Data

Feb. 17, 1995 [JP] Japan ................ 7-29167

[51] Int. Cl.$^6$ .................. C12Q 1/60; C12Q 1/26; C12Q 1/00; G01N 33/92
[52] U.S. Cl. .................. 435/11; 435/25; 435/20; 435/4; 436/71; 436/63; 423/522; 556/51; 552/544
[58] Field of Search ............ 435/25, 11, 20, 435/4; 436/71, 63; 423/522; 556/51; 552/544

[56] References Cited

U.S. PATENT DOCUMENTS 5,597,703  1/1997  Murakami .................. 435/25

OTHER PUBLICATIONS

Slotte et al; Biochim. Biophys. Acta; vol. 1145 (No. 2), pp. 243–249; (1993), month not available.

*Primary Examiner*—Louise Leary
*Attorney, Agent, or Firm*—Young & Thompson

[57] ABSTRACT

A method for determination of activity of a cholesterol oxidase comprises the following steps. A monomolecule film comprising a sterol and a phospholipid is formed on a surface of a cholesterol oxidase solution. Subsequently, a surface pressure of the monomolecule film is measured in order to find a rate of increase in the surface pressure of the monomolecule film where a magnitude of the activity of the cholesterol oxidase is defined by the rate of increase in the surface pressure.

9 Claims, 3 Drawing Sheets

METHOD AND APPARATUS FOR DETERMINATION OF THE ACTIVITY OF CHOLESTEROL OXIDASE AND METHOD AND APPARATUS FOR EVALUATION OF THE TOXICITY OF CHEMICAL SUBSTANCES

BACKGROUND OF THE INVENTION

1. Field of the Invention

The present invention relates to a method and an apparatus for determination of the activity of cholesterol oxidase, which utilizes a gas-liquid surface mono-molecule film, and further relates to a method and an apparatus for evaluation of the toxicity of chemical substances, which also utilizes a gas-liquid surface monomolecular film.

2. Description of the Related Art

The conventional determination method for the activity of the cholesterol oxidase has been known as a biochemical analysis method for cholesterol oxidase to be used for causing quantitative reaction of cholesterol which is one of the clinical laboratory items. The following method is disclosed in Methods of Enzymatic Aualysis, vol. 1, Fundamentals, 3rd. ed., 1983. As shown in the following formula (1), cholesterol is oxidized in the presence of cholesterol oxidase to generate cholestenon and hydrogen peroxide.

A first conventional method for determination of the activity of cholesterol oxidase is to subject hydrogen peroxide generated by the above oxidizing reaction to an UV measurement.

A second conventional method for determination of the activity of cholesterol oxidase is as follows. Methanol is oxidized by both catalase and hydrogen peroxide generated by the above oxidizing reaction to generate formaldehyde which is then reacted with both acetylacetone and ammonia to thereby generate 3,5-diacetyl-1,4-dihydrolutidine which is subsequently subjected to a measurement of its absorbency in a wavelength in the range of 405–415 nm.

A third conventional method for determination of the activity of cholesterol oxidase is as follows. Hydrogen peroxide generated by the above oxidizing reaction is reacted in the presence of peroxidase with phenol and 4-aminoantipyrine to generate a coloring matter which is then subjected to a measurement of its absorbency in a wavelength in the range of 600 nm.

A fourth conventional method for determination of the activity of cholesterol oxidase is as follows. Hydrogen peroxide generated by the above oxidizing reaction is reacted in the presence of peroxidase with 3-methyl-2-benzothiazolinonhydrazone and dimethylaniline to generate a coloring matter which is then subjected to a measurement of its absorbency in a wavelength in the range of 600 nm.

A fifth conventional method for determination of the activity of cholesterol oxidase is as follows. Hydrogen peroxide generated by the above oxidizing reaction is reacted in the presence of peroxidase with 2,2'-azino-di-[3-ethylbenzthiazoline-sulfonic acid] ABTS to generate a cation radical which is then subjected to a measurement of its absorbency in a wavelengah in the range of 420–436 nm.

A sixth conventional method for determination of the activity of cholesterol oxidase is as follows. Luminol is oxidized by hydrogen peroxide generated by the above oxidizing reaction in the presence of peroxidase to generate a chemical luminance energy to be measured.

The above conventional determination methods have the following disadvantages. Since cholesterol is insoluble to water, surface active agent is used for dispersing cholesterol as substrate in water for determination of the activity of the cholesterol oxidase. The activity to be determined is an activity of the cholesterol oxidase to cholesterol in the presence of the surface active agent. Needless to say, the activity of the cholesterol oxidase to cholesterol in the presence of the surface active agent depends upon the surface active agent. The conventional method using the surface active agent, enzymes and coloring matters require complicated operations.

A conventional method for evaluation of the chemical substance toxicity is carried out by using mammals except for human, animal cells and microorganisms in order to predict toxic influences-to-human of chemical substances since it is impossible to subject human to a direct test of toxicity influence of chemical substances to human. Actually, evaluations in the toxicity-to-human are carried out for medicine, food additive, industrial waste, biological products and the like. The above toxicity includes the general toxicity such as acute toxicity, short-period toxicity and long-period toxicity as well as specific toxicity such as variability, local stimulation, allergy, tumor igenicity, teratogenicity and reproducitvity, and additionally ensequestration such as breath, metabolism, accumulation, discharge, and yet additionally biological, pharmacological and cytological toxicity.

In the Japanese patent publication No. 5-74358, the following cytological toxicity test is disclosed. Fluorescent substance and medication are introduced into cells which are on culturing so that a variation in fluorescence in cells is analyzed to determine indication for sensibility of cells to medication.

If the conventional evaluation method for the toxicity of the chemical substances uses the animals, then it is required to breed the animals to be tested, for which reason this method is expensive, time-consuming and trouble-some. This method is not preferable from the zoophilic viewpoint. If the cells are used, it is required to culture the cells. This method is also time-consuming and trouble-some. For those reasons, the conventional toxicity evaluation method would be a complicated and time-consuming procedure.

SUMMARY OF THE INVENTION

Accordingly, it is an object of the present invention to provide a novel method for determination of the activity of cholesterol oxidase to cholesterol without using any surface active agent.

It is a further object of the present invention to provide a simple method for determination of the activity of cholesterol oxidase to cholesterol.

It is a further-more object of the present invention to provide a method for determination of the activity of cholesterol oxidase to cholesterol, which is free from any time-consuming procedure.

It is another object of the present invention to provide a novel method for evaluation of the toxicity of chemical substances without using any experimental animals and cells.

It is yet another object of the present invention to provide a simple method for evaluation of the toxicity of chemical substances without using any experimental animals and cells.

It is still another object of the present invention to provide a method for evaluation of the toxicity of chemical substances without using any experimental animals and cells, which is free from any time-consuming procedure.

It is an additional object of the present invention to provide a novel apparatas for determination of the activity of cholesterol oxidase to cholesterol without using any surface active agent.

It is a further additional object of the present invention to provide a simple apparatus for determination of the activity of cholesterol oxidase to cholesterol.

It is a further more additional object of the present invention to provide a apparatus for detemination of the activity of cholesterol oxidase to cholesterol, which is free from any time-consuming procedure.

It is another additional object of the present invention to provide a novel apparatus for evaluation of the toxicity of chemical substances without using any experimental animals and cells.

It is yet another additional object of the present invention to provide a simple apparatus for evaluation of the toxicity of chemical substances without using any experimental animals and cells.

It is still another additional object office present invention to provide an apparatus for evaluation of the toxicity of chemical substances without using any experimental animals and cells, which is free from any time-consuming procedure.

The above and other objects, features and advantages of the present invention will be apparent from the following descriptions.

The present invention provides a method for determination of activity of a cholesterol oxidasc comprising the following steps. A monomolecule film comprising a sterol and a phospholipid is formed on a surface of a cholesterol oxidase solution. Subsequently, a surface pressure of the monomolecule film is measured in order to find a rate of increase in the surface pressure of the monomolecule film where a magnitude of the activity of the cholesterol oxidase is defined by the rate of increase in the surface pressure.

The present invention also provides a method for evaluation of toxicity of a chemical substance which has an ability to reduce activity of a cholesterol oxidase, comprising the following steps. A monomolecule film comprising a sterol and a phospholipid is formed on a surface of a cholesterol oxidase solution added with a chemical substance. Subsequently, a surface pressure of the monomoleculc film is measured in order to find a rate of increase in the surface pressure of the monomolecule film where a magnitude of the activity office cholesterol oxidase is defined by the rate of increase in the surface pressure. The rate of increase in the surface pressure measured is compared to a reference rate wherein the reference rate has previously been found by measuring a surface pressure of the monomolecule film formed on a surface of the cholesterol oxidase solution free of the chemical substance.

The present invention further provides an apparatus for determination of activity of a cholesterol oxidase comprising the following elements. A trough is provided, which has at least a cell which contains a cholesterol oxidase solution. A dropping unit is provided over the trough for dropping a monomolecule film developing solution onto a surface of the cholesterol oxidase solution in order to form a monomolecule film comprising a sterol and a phospholipid on the surface of the cholesterol oxidase solution. A measuring unit is provided over the trough and spaced apart from the dropping unit for measuring a surface pressure of the monomolecule film. A computing unit being electrically coupled to at least the measuring unit for receiving information of the surface pressure measured from the measuring unit in order to compute a rate of increase in the surface pressure of the monomolecule film and then compute a magnitude of the activity of the cholesterol oxidase on the basis of the rate computed.

The present invention also provides an apparatus for evaluation of toxicity of a chemical substance which has an ability to reduce activity of a cholesterol oxidase, comprising the following elements. A trough is provided, which has at least a cell which contains a cholesterol oxidase solution. A dropping unit is provided over the trough for dropping a monomolecule film developing solution onto a surface of the cholesterol oxidase solution in order to form a monomolecule film comprising a sterol and a phospholipid on the surface of the cholesterol oxidase solution. A measuring unit is provided over the trough and spaced apart from the dropping unit for measuring a surface pressure of the monomolecule film. A computing unit is electrically coupled to at least the measuring unit for receiving infomation of the surface pressure measured from the measuring unit in order to compute a rate of increase in the surface pressure of the monomolecule film and then compares the rate measured to a reference rate already stored in the computing unit, wherein the reference rate has previously been found by measuring a surface pressure of the monomolecule film formed on a surface of the cholesterol oxidase solution free of the chemical substance.

BRIEF DESCRIPTIONS OF THE DRAWINGS

Preferred embodiments of the present invention will be described in detail with reference to the accompanying drawings.

DESCRIPTION OF THE PREFERRED EMOBIDIMENT

Figure 1:
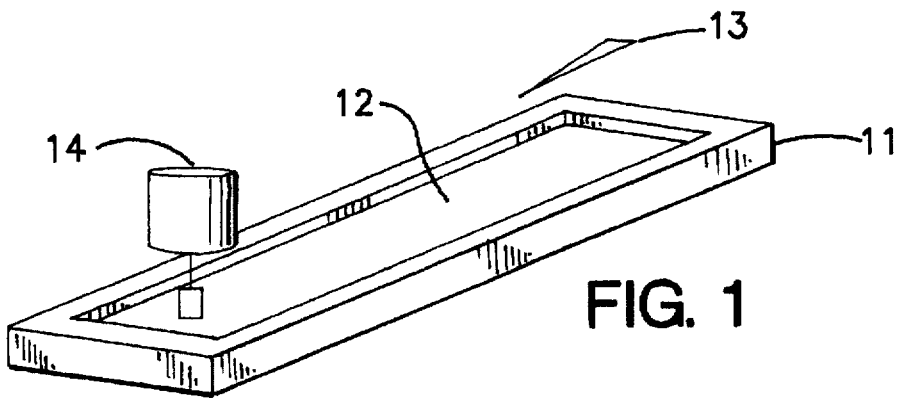
FIG. 1 is a perspective view illustrative of an apparatus for forming a monomolecule film and subsequent measuring a surface pressure thereof according to the present invention.

The present invention provides a method for determination of activity of a cholesterol oxidase comprising the following steps. A monomolecule film comprising a sterol and a phospholipid is formed on a surface of a cholesterol oxidase solution. Subsequently, a surface pressure of the monomolecule film is measured in order to find a rate of increase in the surface pressure of the monomolecule film where a magnitude of the activity of the cholesterol oxidase is defined by the rate of increase in the surface pressure.

The surface pressure of the monomolecular film may be measured by measuring a surface tension of the monomolecule film.

Also, the monomolecule film maybe formed by dropping a monomolecule film developing solution onto the surface of the cholesterol oxidase solution.

Additionally cholesterol oxidase solution may be a buffer solution including N-2-hydroxyethylpiperazine-N'-2-ethane sulfuric acid, where the ion strength is 0.1 and pH value is 7.45 as well as the cholesterol oxidase is dissolved in the buffer solution, and that the monomolecule film development solution includes 70 mol % of L-α-dimyristylphosphatizircoline and 30 mol % of cholesterol.

The cholesterol oxidas solution may be a buffer solution including N-2-hydroxyethylpiperazine-N'-2-ethane sulfuric acid, where the ion strenght is 0.1 and pH value is 7.45 as well as the cholesterol oxidase is dissolved in the buffer solution, and wherein the monomolecule film development solution includes 70 mol % of L-α-dipalmytylphosphatizircoline and 30 mol % of dihydrocholesterol.

The cholesterol oxidase solution, may be a buffer solution including N-2-hydroxyethylpiperazine-N'-2-ethane sulfuric acid, where the ion strength is 0.1 and pH value is 7.45 as well as the cholesterol oxidase is dissolved in the buffer solution, and wherein the monomolecule film development solution includes 70 mol % of L-α-di-palmytylphosphatizirethanol amine and 30 mol % of pregnenolone.

The present invention also provides a method of evaluation of toxicity of a chemical substance which has an ability to reduce acitvity of a cholesterol oxidase, comprising the follwoing steps. A monomolcule film comprising a sterol and a phospholipid is formed on a surface of a cholesterol oxidase solution added with a chemical substance. Subsequently, a surface pressure of a monomolecule film is measured in order to find a rate of increase in the surface pressure of the monomolecule film where a magnitude of the activity of the cholesterol oxidase is defined by the rate of increase in the surface pressure. The rate of increase in the surface pressure measured is compared to a reference rate wherein the reference rate has previously been found by measuring a surface pressure of the monomolecule film formed on a surface of the cholesterol oxidase solution free of the chemical substance.

The surface pressure of the monomolecular film may be measured by measuring a surface tension of the monomolecule film.

The monomolecule film may be formed by dropping a monomolecule film developing solution onto the surface of the cholesterol oxidase solution.

The cholesterol oxides solution may be a buffer solution including N-2-hydroxyethylpiperazine-N'-2-ethane sulfuric acid, where the ion strength is 0.1 and pH value is 7.45 as well as the cholesterol oxidase is dissolved in the buffer solution, and wherein the monomolecule film development solution includes 70 mol % of L-α-dimyristylphosphatizircolinc and 30 mol% of cholesterol.

The cholesterol oxides solution may be a buffer solution including N-2-hydroxyethylpiperazine-N'-2-ethanc sulfuric acid, where the ion strength is 0.1 and pH value is 7.45 as well as the cholesterol oxidase is dissolved in the buffer solution, and wherein the monomolecule film development solution includes 70 mol % of L-α-dipalmytylphosphatizircoline and 30 mol % of dihydrocholesterol.

The cholesterol oxides solution may be a buffer solution including N-2-hydroxyethylpiperazine-N'-2-ethane sulfuric acid, where the ion strength is 0.1 and pH value is 7.45 as well as the cholesterol oxidase is dissolved in the buffer solution, and wherein the monomolecule film development solution includes 70 mol % of L-α-di-palmytylphosphatizirethanol amine and 30 mol % of pregnenolone.

The present invention further provides an apparatus for determination of activity of a cholesterol oxidase comprising the following elements. A trough is provided, which has at least a ccll which contains a cholesterol oxidase solution. A dropping unit is provided over the trough for dropping a monomolecule film developing solution onto a surface of the cholesterol oxidase solution in order to form a monomolecule film comprising a sterol and a phospholipid on the surface of the cholesterol oxidase solution. A measuring unit is provided over the trough and spaced apart from the dropping unit for measuring a surface pressure of the monomolecule film. A computing unit being electrically coupled to at least the measuring unit for receiving information of the surface pressure measured from the measuring unit in order to compute a rate of increase in the surface pressure of the monomolecule film and then compute a magnitude of the activity of the cholesterol oxidase on the basis of the rate computed.

It is available to further provide at least a movable partition plate over the trough for partition of the cholesterol oxidase solution into a primary part and a subordinate part, wherein the surface pressure of the monomolecule film formed on the primary part is measured, and also provide a partition plate controller coupled to the movable partition plate for control movements of rise movable partition plate so as to set a surface area of the primary part at a predetermined value. In this case, the computing unit may compute a position of the movable partition plate on the basis of the predetermined value of the surface area of the primary part, and the partition plate controller is electrically coupled to the computing unit for receiving information of the position computed from the computing unit.

The measuring unit may comprise a surface tensiometer for measuring a surface tension of the monomolecule film, and wherein the computing unit computes the surface pressure on the basis of the surface tension measured by the surface tensiometer.

There may be further provided a movable stage provided under the trough for mechanically supporting and moving the trough in a horizontal plane, and also provide a stage controller coupled to both the stage for control movement of the stage. The stage controller is also electrically coupled to the computing unit for receiving information of the movement of the stage. In this case, it is available that the trough has a rectangular shape and the movable stage moves the trough on the basis of X-Y coordinates. Alternatively, the trough may have a circular shape and has a plurality of cells which are circumferentially aligned and different monomolecule films are formed, and the movable stage rotates the trough.

The present invention also provides an apparatus for evaluation on toxicity of a chemical substance which has an ability to reduce activity of a cholesterol oxidase, comprising the following elements. A trough is provided, which has at least a cell which contains a cholesterol oxidase solution.

A dropping unit is provided over the trough for dropping a monomolecule film developing solution onto a surface of the cholesterol oxidase solution in order to form a monomolecule film comprising a sterol and a phospholipid on the surface of the cholesterol oxidase solution. A measuring unit is provided over the trough and spaced apart from the dropping unit for measuring a surface pressure of the monomolecule film. A computing unit is electrically coupled to at least the measuring unit for receiving information of the surface pressure measured from the measuring unit in order to compute a rate of increase in the surface pressure of the monomolecule film and then compares the rate measured to a reference rate already stored in the computing unit, wherein the reference rate has previously been found by measuring a surface pressure of the monomolecule film formed on a surface of the cholesterol oxidase solution free of the chemical substance.

There may be further provided at least a movable partition plate over the trough for partition the cholesterol oxidase solution into a primary part and a subordinate part, wherein the surface pressure of the monomolecule film formed on the primary part is measured, and also provide a partition plate controller coupled to the movable partition plate for control movements of the movable partition plate so as to set a surface area of the primary part at a predetermined value. In this case, the computing unit may compute a position of the movable partition plate on the basis of the predetermined value of the surface area of the primary part, and the partition plate controller is electrically coupled to the computing unit for receiving information of the position computed from the computing unit.

The measuring unit may comprise a surface tensiometer for measuring a surface tension of the monomolecule film, and wherein the computing unit computes the surface pressure on the basis of the surface tension measured by the surface tensiometer.

There may be further provided a movable stage provided under the trough for mechanically supporting and moving the trough in a horizontal plane, and also a stage controller coupled to both the stage for control movement of the stage. The stage controller is also electrically coupled to the computing unit for receiving information of the movement of the stage. In this case, it is available that the trough has a rectangular shape and the movable stage moves the trough on the basis of X-Y coordinates. Alternatively, the trough may have a circular shape and a plurality of cells which are circumferentially aligned and different monomolecule films are formed, and the movable stage rotates the trough.

EXAMPLES

Figure 2:
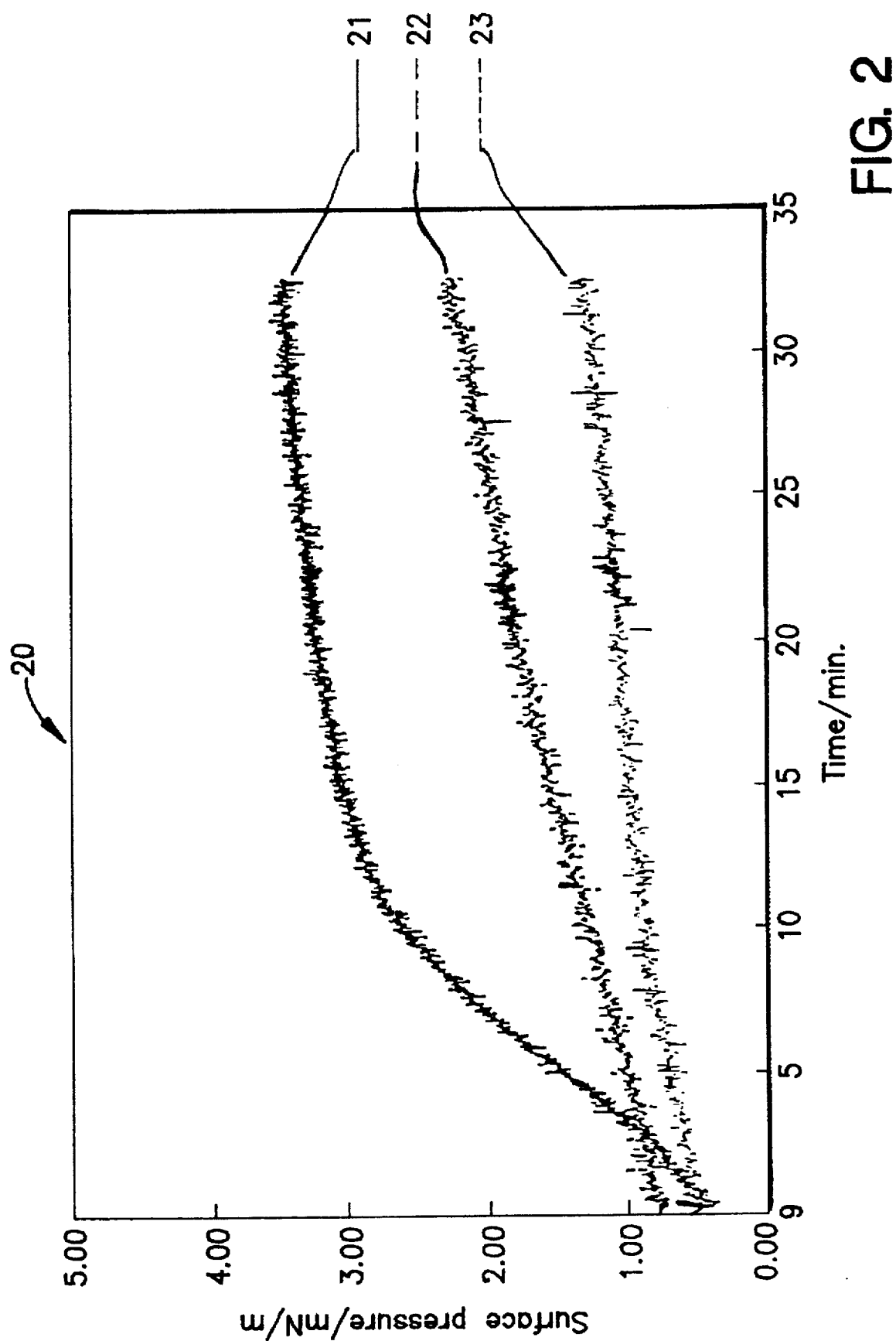
FIG. 2 is a diagram illustrative of measured surface pressure of monomolecule film versus time according to the present invention.

According to the present invention, a monomolecule film development solution 13 is dropped on a surface of a cholesterol oxidase solution 12 to form a monomolecule film on the surface of the cholesterol oxidase solution 12. A surface tension of the monomolecule film is measured by a surface-tensiometer 14. The measured variations in surface tensions of the monomolecule films versus time are shown in FIG. 2. A curve 21 represents a variation in a surface tension of a monomolecule film formed on a surface of a cholesterol oxidase solution 12 of 5 mU/ml. A curve 22 represents a variation in a surface tension of a monomolecule film prepared on a surface of a cholesterol oxidase solution 12 of 1 mU/ml. A curve 23 represents a variation in a surface tension of a monomolecule film prepared on a surface of a cholesterol oxidase solution of 1 mU/ml in which 10 micro-Mol of lead acetate is dissolved. The surface pressure of the monomolecule film is gradually increased after the monomolecule film is prepared, wherein the increasing rate depends upon the cholesterol oxidase activity and the presence of toxicity substance.

(Example 1)

A first present invention directed to a method for determination in the activity of the cholesterol oxidase will be described with reference to a first example as follows.

As the cholesterol oxidase solution 12, there was used a buffer solution including N-2-hydroxyethylpiperazine-N'-2-ethane sulfuric acid, where the ion strength is 0.1 and pH value is 7.45 as well as 1 mU/ml and 5 mU/ml of the cholesterol oxidase are dissolved in the buffer solution. As the monomolecule film development solution 13, there was used a monomolecule film development solution comprising 70 mol % of L-α-dimyristylphosphatizircoline and 30 mol % of cholesterol.

10 micro-1 of the monomolecule film development solution 13 was dropped on to a surface of 45 $cm^2$ of the cholesterol oxidase solution 12 of 5 mU/ml to form a monomolecule film on the surface of the cholesterol oxidase solution 12. A surface pressure of the monomolecule film was measured by a surface tensiometer 14 to obtain the curve 21 shown in FIG. 2. The surface pressure of the monomolecule film was gradually increased after the monomolecule film was prepared. As shown by the curves 21 and 22, the increasing rate depends upon the cholesterol oxidase activity.

TABLE 1

| Curves | Cholesterol Oxidase (mU/ml) | Lead Acetate (μ Mol) | Linear Differential Coefficient (mN/mmin.) |
|---|---|---|---|
| 21 | 5 | 0 | $25.5 \times 10^{-2}$ |
| 22 | 1 | 0 | $5.5 \times 10^{-2}$ |
| 23 | 1 | 10 | $4.2 \times 10^{-2}$ | where the linear differential coefficient represents the rate of increase in the surface pressure of the monomolecule film. As described above, the activity of the cholesterol oxidase depends upon the rate of increase in the surface pressure of the monomolecule film. This means that the rate of increase in the surface pressure of the monomolecule film represents the activity of the cholesterol oxidase. Accordingly, the ratio of the linear differential coefficient represents of the curves 21 and 22 represents the ratio the activities of the cholesterol oxidase. At five minutes after the monomolecule film was prepared, the curve 21 has a linear differential coefficient which is larger five times than a linear differential coefficient of the curve 22. This means that the cholesterol oxidase of the curve 21 has an activity which is five times larger than an activity of the curve 22 since the linear differential coefficient represents the rate in the increase of the surface pressure, and wherein the rate in the increase of the surface pressure represents the activity of the cholesterol oxidase as described above.

For the above reason, according to the present invention, the monomolecule film development solution 13 is dropped onto a surface of an unknown cholesterol oxidase solution 12 in order to form a monomolecule film on the surface of the unknown cholesterol oxidase solution 12 so that the surface pressure of the monomolecule film is measured to determine the activity of an unknown cholesterol oxidase included in the unknown cholesterol oxidase solution 12. In order to improve accuracy in the determination of the activity of the cholesterol oxidase, it is effective to previously measure the surface pressure of the already-known cholesterol oxidase activity and then prepare analytical curves on the basis of the measured surface pressure.

A second present invention directed to a method for evaluation on the toxicity of chemical substances will be described with reference to the following second to sixth examples. Any chemical substrance to be evaluated on the toxicity is previously dissolved or dispersed in the cholesterol oxidase solution 12. A monomolecule film is formed on a surface of the cholesterol oxidase solution 12 by use of a monomolecule film development solution including any phospholipid and any sterol. The surface pressure of the monomolecule film is measured to find a rate in the increase of the surface pressure of the monomolecule film. If the toxicitic chemical substance is dissolved in the cholesterol oxidase solution 12, then the toxicity thereof reduces the activity of the cholesterol oxidase dissolved in the cholesterol oxidase solution 12. The reduction in the activity of the cholesterol oxidase results in a reduction in the increasing rate of the surface pressure of the monomolecule film. If the measured increasing rate of the surface pressure of the monomolecule film is smaller than that in case of the toxicity free solution, this demonstrates that the activity of the cholesterol oxidase dissolved in the cholesterol oxidase solution is reduced by the toxicity of the toxicitic chemical substance dissolved in the cholesterol oxidase solution. This means that the toxicitic chemical substance would be present in the cholesterol oxidase solution.

(Example 2)

As a cholesterol oxidase solution 12, there was used a buffer solution including N-2-hydroxyethylpiperzane-N'-2-ethane sulfuric acid, where the ion strength is 0.1 and pH value is 7.45 as well as 1 mU/ml of the cholesterol oxidase is dissolved in the buffer solution. In the buffer solution, 10 micro-M of lead acetate as a toxicitic chemical substance was dissolved. As a monomolecule film development solution 13, there was used a monomolecule film development solution comprising 70 mol % of L-α-dimyristylphosphatizircoline and 30 mol % of cholesterol.

10 micro-1 of the monomolecule film development solution 13 was dropped onto a surface of 45 cm² of the cholesterol oxidase solution 12 of 1 mU/ml, into which 10 micro-M of lead acetate as a toxicitic chemical substance was dissolved, in order to form a monomolecule film on the surface of the cholesterol oxidase solution 12. A surface pressure of the monomolecule film was measured by a surface tensiometer 14 to obtain a curve 23 shown in FIG. 2 and on Table 1. The surface pressure of the monomolecule film was gradually increased after the monomolecule film was prepared. The increasing rate of the surface pressure of the monomolecule film depends upon file cholesterol oxidase activity. As described above, the activity of the cholesterol oxidase depends upon the rate of increase in the surface pressure of the monomolecule film. This means that the rate of increase in the surface pressure of the monomolecule film represents the activity of the cholesterol oxidase. At five minutes after the monomolecule film was prepared, the curve 23 has a linear differential coefficient which is smaller than the linear differential coefficient of the curve 22. This means that the cholesterol oxidase of the curve 23 has an activity which is smaller than the activity of the curve 22. This proves that the lead acetate acts as a toxicitic chemical substrance which reduces the activity of the cholesterol oxidase.

For the above reason, the monomolecule film development solution 13 is dropped onto a surface of a cholesterol oxidase solution 12, into which any toxicity chemical substance is dissolved, in order to form a monomolecule film on the surface of the cholesterol oxidase solution 12. The surface pressure of the monomolecule film is measured to confirm the presence of any toxicity chemical substance dissolved in the cholesterol oxidase solution 12. If the toxicitic chemical substance is dissolved in the cholesterol oxidase solution 12, then the toxicity thereof reduces the activity of the cholesterol oxidase dissolved in the cholesterol oxidase solution 12. The reduction in the activity of the cholesterol oxidase results in a reduction in the increasing rate of the surface pressure of the monomolecule film. If the measured increasing rate of the surface pressure of the monomolecule film is smaller than that in case of the toxicity free solution, this demonstrates that the activity of the cholesterol oxidase dissolved in the cholesterol oxidase solution is reduced by the toxicity of the toxicitic chemical substance dissolved in the cholesterol oxidase solution. This means that the toxictic chemical substance would be present in the cholesterol oxidase solution.

(Example 3)

As a cholesterol oxidase solution 12, there was used a buffer solution including N-2-hydroxyethylpiperazine-N'-2-ethane sulfuric acid, where the ion strength is 0.1 and pH value is 7.45 as well as 1 mU/ml of the cholesterol oxidase is dissolved in the buffer solution. In the buffer solution, 10 micro-M of zinc chloride as a toxicitic chemical substance was dissolved. As a monomolecule film development solution 13, there was used a monomolecule film development solution comprising 70 mol % of L-α-dimyristylphosphatizircoline and 30 mol % of cholesterol.

10 micro-1 of the monomolecule film development solution 13 was dropped onto a surface of 45cm² of the cholesterol oxidase solution 12 of 1 mU/ml, into which 10 micro-M of zinc chloride as a toxicitic chemical substance was dissolved, in order to form a monomolecule film on the surface of the cholesterol oxidase solution 12. A surface pressure of the monomolecule film was measured by a surface tensiometer 14 to obtain a curve 23 shown in FIG. 2 and on Table 1. The surface pressure of the monomolecule film was gradually increased after the monomolecule film was prepared. The increasing rate of the surface pressure of the monomolecule film depends upon the cholesterol oxidase activity. As described above, the activity of the cholesterol oxidase depends upon the rate of increase in the surface pressure of the monomolecule film. This means that the rate of increase in the surface pressure of the monomolecule film represents the activity of the cholesterol oxidase. At five minutes after the monomolecule film was prepared, the curve 23 has a linear differential coefficient which is smaller than the linear differential coefficient of the curve 22. This means that the cholesterol oxidase of the curve 23 has an activity which is smaller than the activity of the curve 22. This proves that the zinc chloride acts as a toxicitic chemical substance which reduces the activity of the cholesterol oxidase.

For the above reason, the monomolecule film development solution 13 is dropped onto a surface of a cholesterol oxidase solution 12, into which any toxicity chemical substance is dissolved, in order to form a monomolecule film on the surface of the cholesterol oxidase solution 12. The surface pressure of the mononmolecule film is measured to confirm the presence of any toxicity chemical substance dissolved in the cholesterol oxidase solution 12. If the toxicitic chemical substance is dissolved in the cholesterol oxidase solution 12, then the toxicity thereof reduces the activity of the cholesterol oxidase dissolved in the cholesterol oxidase solution 12. The reduction in the activity of the cholesterol oxidase results in a reduction in the increasing rate of the surface pressure of the monomolecule film. If the measured increasing rate of the surface pressure of the monomolecule film is smaller than that in case of the toxicity free solution, this demonstrates that the activity of the cholesterol oxidase dissolved in the cholesterol oxidase solution is reduced by the toxicity of the toxicitic chemical substance dissolved in the cholesterol oxidase solution. This means that the toxicitic chemical substance would be present in the cholesterol oxidase solution.

(Example 4)

As a cholesterol oxidase solution 12, there was used a buffer solution including N-2-hydroxyethylpiperazine-N'-2-ethane sulfuric acid, where the ion strength is 0.1 and pH value is 7.45 as well as 1 mU/ml of the cholesterol oxidase is dissolved in the buffer solution. In the buffer solution, 10 micro-M of calcium chloride as a toxicitic chemical substance was dissolved. As a monomolecule film development solution 13, there was used a monomolecule film development solution comprising 70 mol % of L-α-dimyristylphosphatizircoline and 30 mol % of cholesterol.

10 micro-1 of the monomolecule film development solution 13 was dropped onto a surface of 45 cm$^2$ of the cholesterol oxidase solution 12 of 1 mU/ml, into which 10 micro-M of calcium chloride as a toxicitic chemical substance was dissolved, in order to form a monomolecule film on the surface of the cholesterol oxidase solution 12. A surface pressure of the monomolecule film was measured by a surface tensiometer 14 to obtain the same curve as the curve 22 shown in FIG. 2 and on Table 1. This means that calcium chloride has no toxicity.

(Example 5)

As a cholesterol oxidase solution 12, there was used a buffer solution including N-2-hydroxyethylpiperazine-N'-2-ethane sulfufic acid, where the ion strength is 0.1 and pH value is 7.45 as well as 1 mU/ml of the cholesterol oxidase is dissolved in the buffer solution. In the buffer solution, 10 micro-M of mercury chloride as a toxicitic chemical substance was dissolved. As a monomolecule film development solution 13, there was used a monomolecule film development solution comprising 70 mol % of L-α-dipalmytylphosphatizircoline and 30 mol % of dihydrocholesterol.

10 micro-1 of the monomolecule film development solution 13 was dropped onto a surface of 45 cm$^2$ of the cholesterol oxidase solution 12 of 1 mU/ml, into which 10 micro-M of mercury chloride as a toxicitic chemical substance was dissolved, in order to form a monomolecule film on the surface of the cholesterol oxidase solution 12. A surface pressure of the monomoleoule film was measured by a surface tensiometer 14 to obtain the same curve as the curve 23 shown in FIG. 2 and on Table 1. The surface pressure of the monomolecule film was gradually increased after the monomolecule film was prepared. The increasing rate of the surface pressure of the monomolecule film depends upon the cholesterol oxidase activity. As described above, the activity of the cholesterol oxidase depends upon the rate of increase in the surface pressure of the monomolecule film. This means that the rate of increase in the surface pressure of the monomolecule film represents the activity of the cholesterol oxidase. At five minutes after the monomolecule film was prepared, the curve 23 has a linear differential coefficient which is smaller than the linear differential coefficient of the curve 22. This means that the cholesterol oxidase of the curve 23 has an activity which is smaller than the activity of the curve 22. This proves that the mercury chloride acts as a toxicitic chemical substance which reduces the activity of the cholesterol oxidase.

For the above reason, the monomolecule film development solution 13 is dropped onto a surface of a cholesterol oxidase solution 12, into which any toxicity chemical substance is dissolved, in order to form a monomolecule film on the surface of the cholesterol oxidase solution 12. The surface pressure of the monomolecule film is measured to confirm the presence of any toxicity chemical substance dissolved in the cholesterol oxidase solution 12. If the toxicitic chemical substance is dissolved in the cholesterol oxidase solution 12, then the toxicity thereof reduces the activity of the cholesterol oxidase dissolved in the cholesterol oxidase solution 12. The reduction in the activity of the cholesterol oxidase results in a reduction in the increasing rate of the surface pressure of the monomolecule film. If the measured increasing rate of the stufface pressure of the monomolecule film is smaller than that in case of the toxicity free solution, this demonstrates that the activity of the cholesterol oxidase dissolved in the cholesterol oxidase solution is reduced by the toxicity of the toxicitic chemical substance dissolved in the cholesterol oxidase solution. This means that the toxicitic chemical substance would be present in the cholesterol oxidase solution.

(Example 6)

As a cholesterol oxidase solution 12, there was used a buffer solution including N-2-hydroxyethylpiperazine-N'-2-ethane sulfuric acid, where the ion strength is 0.1 and pH value is 7.45 as well as 1 mU/ml of the cholesterol oxidase is dissolved in the buffer solution. In the buffer solution, 1 micro-M of sodium dodecylsulfate as a toxicitic chemical substance was dissolved. As a monomolecule film development solution 13, there was used a monomolecule film development solution comprising 70 mol % of L-α-dipalmytylphosphatizir-ethanol and 30mol % of pregnenolone.

10 micro-1 of the monomolecule film development solution 13 was dropped onto a surface of 45 cm$^2$ of the cholesterol oxidase solution 12 of 1 mU/ml, into which 1 micro-M of sodium dodecylsulfate as a toxicitic chemical substance was dispersed, in order to form a monomolecule film on the surface of the cholesterol oxidase solution 12. A surface pressure of the monomolecule film was measured by a surface tensiometer 14 to obtain the same curve as the curve 23 shown in FIG. 2 and on Table 1. The surface pressure of the monomolecule film was gradually increased after the monomolecule film was prepared. The increasing rate of the surface pressure of the monomolecule film depends upon the cholesterol oxidase activity. As described above, the activity of the cholesterol oxidase depends upon the rate of increase in the surface pressure of the monomolecule film. This means that the rate of increase in the surface pressure of the monomolecule film represents the activity of the cholesterol oxidase. At five minutes after the monomolecule film was prepared, the curve 23 has a linear differential coefficient which is smaller than the linear differential coefficient of the curve 22. This means that the cholesterol oxidase of the curve 23 has an activity which is smaller than the activity of the curve 22. This proves that the sodium dodecylsulfate acts as a toxictic chemical substance which reduces the activity of the cholesterol oxidase.

For the above reason, the monomolecule film development solution 13 is dropped onto a surface of a cholesterol oxidase solution 12, into which any toxicity chemical substance is dissolved, in order to form a monomolecule film on the surface of the cholesterol oxidase solution 12. The surface pressure of the monomolecule film is measured to confirm the presence of any toxicity chemical substance dissolved in the cholesterol oxidase solution 12. If the toxicitic chemical substance is dissolved in the cholesterol oxidase solution 12, then the toxicity thereof reduces the activity of the cholesterol oxidase dissolved in the cholesterol oxidase solution 12. The reduction in the activity of the cholesterol oxidase results in a reduction in the increasing rate of the surface pressure of the monomolecule film. If the measured increasing rate of the surface pressure of the monomolecule film is smaller than that in case of the toxicity free solution, this demonstrates that the activity of the cholesterol oxidase dissolved in the cholesterol oxidase solution is reduced by the toxicity of the toxicitic chemical substance dissolved in the cholesterol oxidase solution. This mans that the toxicitic chemical substance would be present in the cholesterol oxidase solution.

A third present invention will be described with reference to seventh to ninth examples, which is directed to an apparatus for both determination in the activity of the cholesterol oxidase and the and evaluation of the toxicity of chemical substances.

(Example 7)

Figure 3:
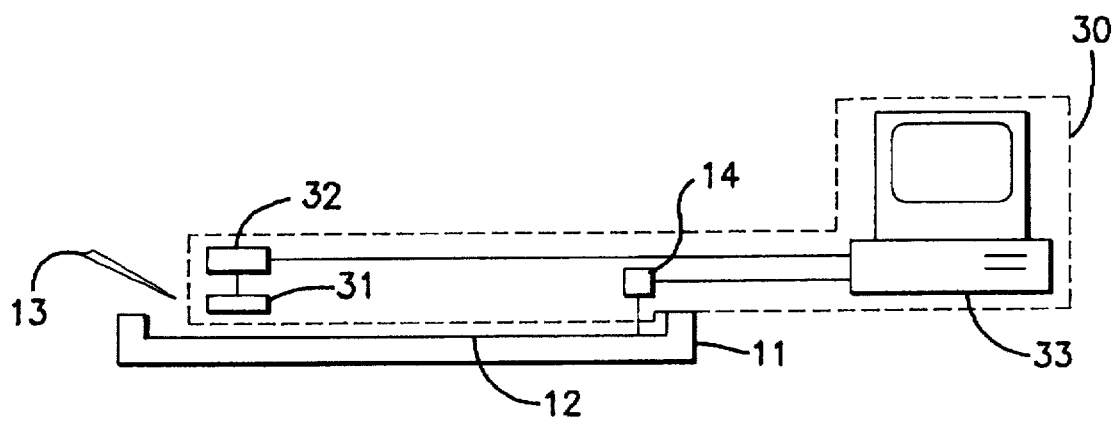
FIG. 3 is a schematic view illustrative of apparatuses for determination of cholesterol oxidase activity and for evaluation of chemical substance toxicity one example according to the present invention.

An apparatus for both determination in the activity of the cholesterol oxidase and the evaluation on the toxicity of chemical substances comprises a trough 11 and a surface tension controller 30. FIG. 3 schematically illustrates the apparatus in this embodiment. The trough 11 receives the cholesterol oxidase solution 12 on which a monomolecule film is formed by dropping a monomolecule film development solution onto the surface thereof. The surface tension controller 30 is provided to set, at a constant value, an initial surface pressure of the monomolecule film at a time when the surface pressure measurement is commenced. The surface tension controller 30 has a partition plate 31 which is positioned over the cholesterol oxidase solution 12. The surface area of the monomolecule film formed on the surface of the cholesterol oxidase solution 12 is defined by the position of the partition plate 31. The position of the partition plate 31 is adjusted by a partition plate positioning controller 32. The partition plate positioning controller 32 is mechanically connected to the partition plate 31 for adjusting the position of the partition plate 31. The partition plate positioning controller 32 is electrically connected to a control unit 33 for receiving electrical information about the surface pressure of the monomolecule film formed on the surface of the cholesterol oxidase solution 12 so as to adjust the position of the partition plate 31 on the basis of the information about the surface pressure from the control unit 33. The control unit 33 is electrically connected to a surface tensiometer 14 which is positioned over the cholesterol oxidase solution 12 and adjusted to measure a surface tension of the monomolecule film formed on the surface of the cholesterol oxidase solution 12. The control unit 33 receives, from the surface tensiometer 14, electrical information about the surface tension of the monomolecule film, which has been measured by the surface tensiometer 14. The monomolecule film development solution 13 is dropped onto a surface of the cholesterol oxidase solution 12 to form the monomolecule film.

As described above, the surface tension controller 30 is provided to control at a constant value the initial surface tension of the monomolecule film at an initial time of the measurement thereof in order to improve accuracy in the measurement of the surface pressure of the monomolecule film. This allows a correct and accurate determination of the activity of the cholesterol oxidase or a correct and accurate evaluation on the toxicity of chemical substance dissolved or dispersed in the cholesterol oxidase solution.

(Example 8)

Figure 4:
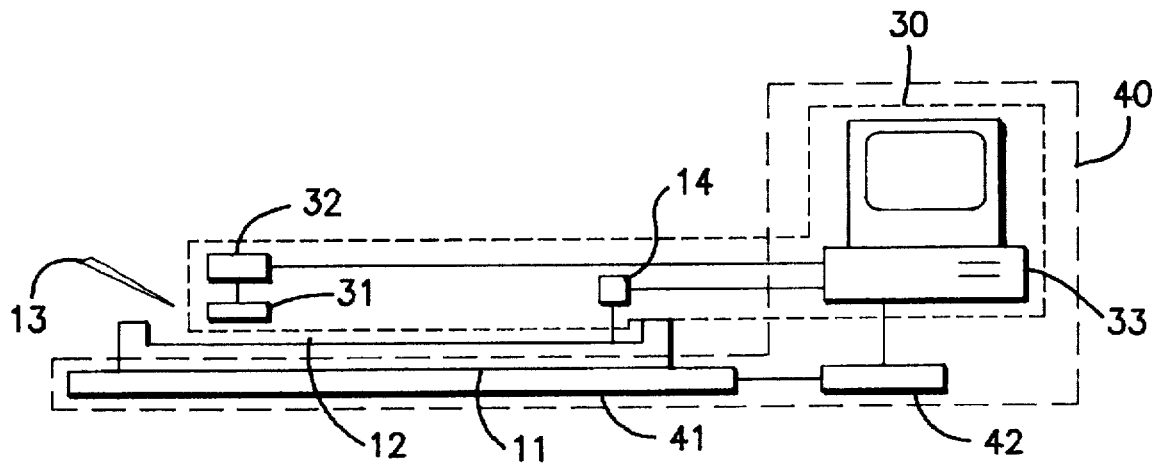
FIG. 4 is a schematic view illustrative of apparatuses for determination of cholesterol oxidase activity and for evaluation of chemical substance toxicity in another example according to the present invention.

An apparatus for both determination in the activity of the cholesterol oxidase and the evaluation on the toxicity of chemical substances comprises not only a trough 11 and a surface tension controller 30 but also a stage control system 40. FIG. 4 schematically illustrates the apparatus in this embodiment. The trough 11 receives the cholesterol oxidase solution 12 on which a monomolecule film is formed by dropping a monomolecule film development solution onto the surface thereof. The surface tension controller 30 is provided to set, at a constant value, an initial surface pressure of the monomolecule film at a time when the surface pressure measurement is commenced. The surface tension controller 30 has a partition plate 31 which is positioned over the cholesterol oxidase solution 12. The surface area of the monomolecule film formed on the surface of the cholesterol oxidase solution 12 is defined by the position of the partition plate 31. The position of the partition plate 31 is adjusted by a partition plate positioning controller 32. The partition plate positioning controller 32 is mechanically connected to the partition plate 31 for adjusting the position of the partition plate 31. The partition plate positioning controller 32 is electrically connected to a control unit 33 for receiving electrical information about the surface pressure of the monomolecule film formed on the surface of the cholesterol oxidase solution 12 so as to adjust the position of the partition plate 31 on the basis of the information about the surface pressure from the control unit 33. The control unit 33 is electrically connected to a surface tensiometer 14 which is positioned over the cholesterol oxidase solution 12 and adjusted to measure a surface tension of the monomolecule film formed on the surface of the cholesterol oxidase solution 12. The control unit 33 receives, from the surface tensiometer 14, electrical information about the surface tension of the monomolecule film, which has been measured by the surface tensiometer 14. The monomolecule film development solution 13 is dropped onto a surface of the cholesterol oxidase solution 12 to form the monomolecule film. The stage control system comprises the above control unit 33, an X-Y stage 41 and an X-Y stage controller 42. The X-Y stage 41 is provided to support the trough 11 so that the trough 11 is placed on the X-Y stage 41. The X-Y stage, on which the trough 11 receiving the cholesterol oxidase solution 12 is placed, is adjusted to move the trough 11 in a horizontal plane along X-axis and Y-axis which are vertical to each other. The X-Y stage may be mechanically connected to the X-Y stage controller 42 so that the X-Y stage can be mechanically moved by the X-Y stage controller 42. Otherwise, the X-Y stage may be electrically connected to the X-Y stage controller 42 for receiving electrical signals as instructions of what amounts of distances the trough 11 should be moved in the X and Y directions so that the X-Y stage can move by itself on the basis of the electrical signals.

As described above, the surface tension controller 30 and the stage control system 40 are provided to control at a constant value the initial surface tension of the monomolecule film at an initial time of the measurement thereof in order to improve accuracy in the measurement of the surface pressure of the monomolecule film. This allows a correct and accurate determination of the activity of the cholesterol oxidase or a correct and accurate evaluation on the toxicity of chemical substance dissolved or dispersed in the cholesterol oxidase solution.

(Example 9)

Figure 6:
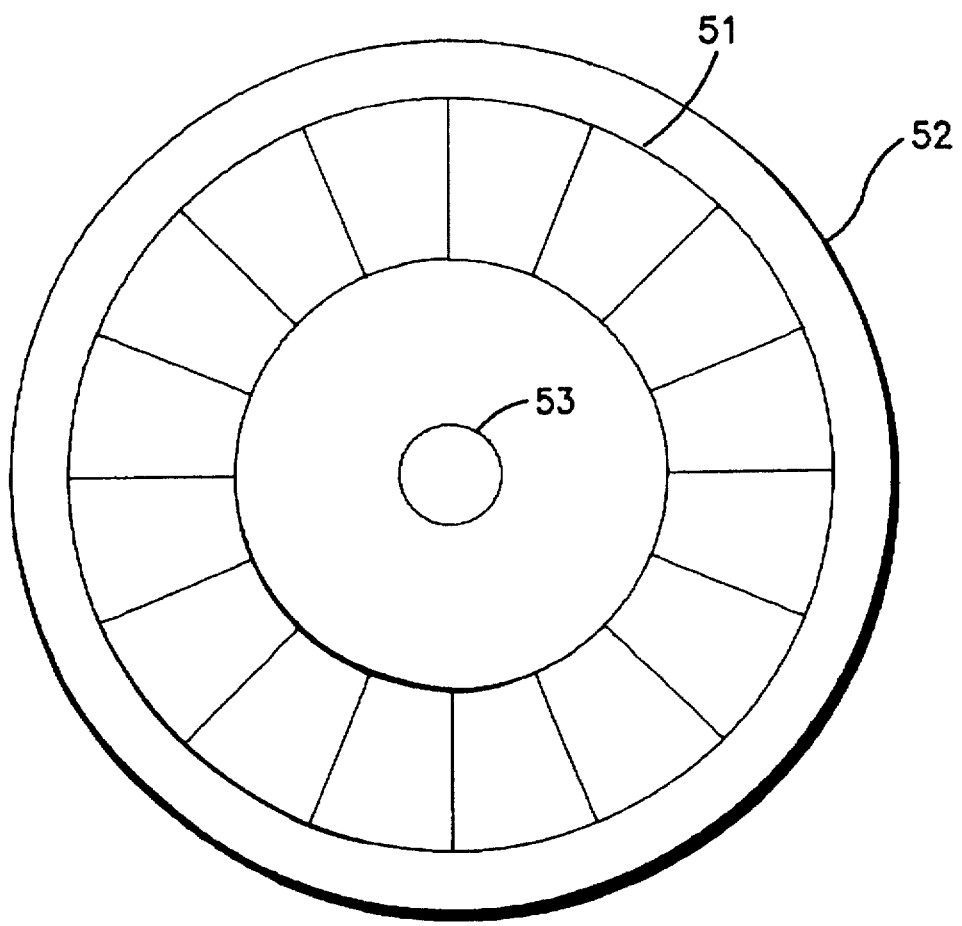
FIG. 6 is a plane view illustrative of a circulation trough, a circulation stage and a stage controller to be used according to the present invention.
Figure 5:
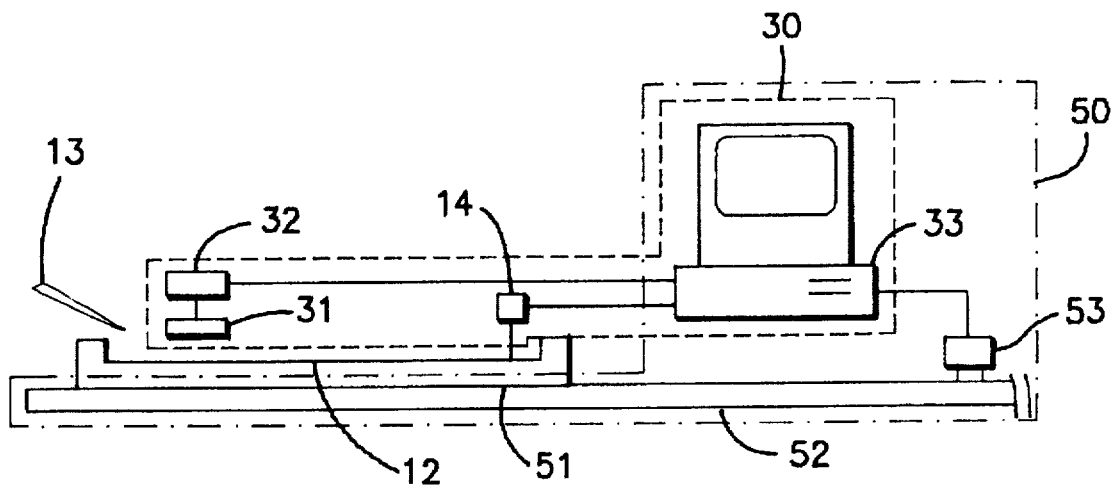
FIG. 5 is a schematic view illustrative of apparatuses for determination of cholesterol oxidase activity and for evaluation of chemical substance toxicity in still another example according to the present invention.

An apparatus for both determination in the activity of the cholesterol oxidase and the evaluation on the toxicity of chemical substances comprises not only a circulation trough 51 and a surface tension controller 30 but also a stage control system 50. FIG. 5 schematically illustrates the apparatus in this embodiment. FIG. 6 is a plane view illustrative of a circulation trough 51, a circulation stage 52 and a circulation stage controller 53. The circulation trough 51 has a plurality of cells, each of which receives the cholesterol oxidase solution 12 on which a monomolecule film is formed by dropping a monomolecule film development solution onto the surface thereof. The surface tension controller 30 is provided to set, at a constant value, an initial surface pressure of the monomolecule film at a time when the surface pressure measurement is commenced. The surface tension controller 30 has a partition plate 31 which is positioned over the cholesterol oxidase solution 12. The surface area of the monomolecule film formed on the surface of the cholesterol oxidase solution 12 is defined by the position of the partition plate 31. The position of the partition plate 31 is adjusted by a partition plate positioning controller 32. The partition plate positioning controller 32 is mechanically connected to the partition plate 31 for adjusting the position of the partition plate 31. The partition plate positioning controller 32 is electrically connected to a control unit 33 for receiving electrical information about the surface pressure of the monomolecule film formed on the surface of the cholesterol oxidase solution 12 so as to adjust the position of the partition plate 31 on the basis of the information about the surface pressure from the control unit 33. The control unit 33 is electrically connected to a surface tensiometer 14 which is positioned over the cholesterol oxidase solution 12 mad adjusted to measure a surface tension of the monomolecule film formed on the surface of the cholesterol oxidase solution 12. The control unit 33 receives, from the surface tensiometer 14, electrical information about the surface tension of the monomolecule film, which has been measured by the surface tensiometer 14. The monomolecule film development solution 13 is dropped onto a surface of the cholesterol oxidase solution 12 to form the monomolecule film. The stage control system 50 comprises the above control unit 33, an circulation stage 52 and an circulation stage controller 53. The circulation stage 52 is provided to support the circulation trough 51 so that the circulation trough 51 is placed on the circulation stage 52. The circulation stage, on which the circulation trough 51 receiving the cholesterol oxidase solution 12 is placed, is adjusted to rotate the circulation trough 51 in a horizontal plane. The circulation stage 52 may be mechanically connected to the circulation stage controller 53 so that the circulation stage 52 can be mechanically rotated by the circulation stage controller 53. Otherwise, the circulation stage 52 may be electrically connected to the circulation stage controller 53 for receiving electrical signals as instructions of what amounts of distances the circulation trough 51 should be rotated in the horizontal plane so that the circulation stage 52 can rotate by itself on the basis of the electrical signals.

As described above, the circulation trough 51 has a plurality of cells which are individually designed to receive different cholesterol oxidase solutions in order to allow short-time determinations of the activity of the different cholesterol oxidase or short-time evaluations on the toxicity of different chemical substances dissolved or dispersed in the cholesterol oxidase solutions. The surface tension controller 30 and the stage control system 50 are provided to control at a constant value the initial surface tension of the monomolecule film at an initial time of the measurement thereof in order to improve accuracy in the measurement of the surface pressure of the monomolecule film. This allows a correct and accurate determination of the activity of the cholesterol oxidase or a correct and accurate evaluation on the toxicity of chemical substance dissolved or dispersed in the cholesterol oxidase solution.

Whereas modifications of the present invention will be apparent to a person having ordinary skill in the art, to which the invention pertains, it is to be understood that embodiments as shown and described by way of illustrations are by no means intended to be considered in a limiting sense. Accordingly, it is to be intended to cover all modifications which fall within the spirit and scope of the following claims directed to the subject mater of the present invention.

What is claimed is:

1. A method for evaluation of toxicity of a chemical substance which has an ability to reduce activity of a cholesterol oxidase, comprising the steps of:

forming a monomolecule film comprising a sterol and a phospholipid on a surface of a cholesterol oxidase solution added with a chemical substance;

measuring a surface pressure of said monomolecule film in order to find a rate of increase in said surface pressure of said monomolecule film where a magnitude of said activity of said cholesterol oxidase is defined by said rate of increase in said surface pressure; and comparing said rate of increase in said surface pressure measured to a reference rate wherein said reference rate has previously been found by measuring a surface pressure of said monomolecule film formed on a surface of said cholesterol oxidase solution free of said chemical substance.

2. The method as claimed in claim 1, wherein said surface pressure of said monomolecule film is measured by measuring a surface tension of said monomolecule film.

3. The method as claimed in claim 2, wherein said monomolecule film is formed by dropping a monomolecule film developing solution onto said surface of said cholesterol oxidase solution.

4. The method as claimed in claim 3, wherein said cholesterol oxidase solution is a buffer solution including N-2-hydroxyethylpiperazine-N'-2-ethane sulfuric acid, where the ion strength is 0.1 and pH value is 7.45 as well as said cholesterol oxidase is dissolved in said buffer solution, and wherein said monomolecule film development solution includes 70 mol % of L-α-dimyristylphosphatizircoline and 30 mol % of cholesterol.

5. The method as claimed in claim 3, wherein said cholesterol oxidase solution is a buffer solution including N-2-hydroxyethylpiperazine-N'-2-ethane sulfuric acid, where the ion strength is 0.1 and pH value is 7.45 as well as said cholesterol oxidase is dissolved in said buffer solution, and wherein said monomolecule film development solution includes 70 mol % of L-α-dipalmytylphosphatizircoline and 30 mol % of dihydrocholesterol.

6. The method as claimed in claim 3, wherein said cholesterol oxidase solution is a buffer solution including N-2-hydroxyethylpiperazine-N'-2-ethane sulfuric acid, where the ion strength is 0.1 and pH value is 7.45 as well as said cholesterol oxidase is dissolved in said buffer solution, and wherein said monomolecule film development solution includes 70 mol % of L-α-di-palmytylphosphatizir-ethanol amine and 30mol % of pregnenolone.

7. A method for determination of activity of a cholesterol oxidase comprising the steps of:

forming a monomolecular film comprising a sterol and a phospholipid on a surface of a cholesterol oxidase solution, wherein said monomolecular film is formed by dropping a monomolecular film developing solution onto said surface of said cholesterol oxidase solution, and wherein said cholesterol oxidase solution is a buffer solution including N-2-hydroxyethylpiperazine-N'-2-ethane sulfuric acid, wherein the ion strength is 0.1 and pH value is 7.45 as well as said cholesterol oxidase is dissolved in said buffer solution, and wherein said monomolecular film development solution includes 70 mol % of L-α-dimyristylphosphatizircoline and 30 mol % of cholesterol, and measuring a surface pressure of said monomolecular film in order to find a rate of increase in said surface pressure of said monomolecular film wherein a magnitude of said activity of said cholesterol oxidase is defined by said rate of increase in said surface pressure.

8. A method for determination of activity of a cholesterol oxidase comprising the steps of:

forming a monomolecular film comprising a sterol and a phospholipid on a surface of a cholesterol oxidase solution, wherein said monomolecular film is formed by dropping a monomolecular film developing solution onto said surface of said cholesterol oxidase solution, and wherein said cholesterol oxidase solution is a buffer solution including N-2-hydroxyethylpiperazine-N'-2-ethane sulfuric acid, wherein the ion strength is 0.1 and pH value is 7.45 as well as said cholesterol oxidase is dissolved in said buffer solution, and wherein said monomolecular film development solution includes 70 mol % of L-α-dipalmytylphosphatizircoline and 30 mol % of dihydrocholesterol, and measuring a surface pressure of said monomolecular film in order to find a rate of increase in said surface pressure of said monomolecular film wherein a magnitude of said activity of said cholesterol oxidase is defined by said rate of increase in said surface pressure.

9. A method for determination of activity of a cholesterol oxidase comprising the steps of:

forming a monomolecular film comprising a sterol and a phospholipid on a surface of a cholesterol oxidase solution, wherein said monomolecular film is formed by dropping a monomolecular film developing solution onto said surface of said cholesterol oxidase solution, and wherein said cholesterol oxidase solution is a buffer solution including N-2-hydroxyethylpiperazine-N'-2-ethane sulfuric acid, wherein the ion strength is 0.1 and pH value is 7.45 as well as said cholesterol oxidase is dissolved in said buffer solution, and wherein said monomolecular film development solution includes 70 mol % of L-α-di-palmytylphosphatizir-ethanol amine and 30 mol % of pregnenolone, and measuring a surface pressure of said monomolecular film in order to find a rate of increase in said surface pressure of said monomolecular film wherein a magnitude of said activity of said cholesterol oxidase is defined by said rate of increase in said surface pressure.

* * * * *